United States Patent [19]
Ma et al.

[11] Patent Number: 5,786,221
[45] Date of Patent: Jul. 28, 1998

[54] DIAGNOSTIC TEST FOR MEASURING ISLET CELL AUTOANTIBODIES AND REAGENTS RELATING THERETO

[75] Inventors: Wai-Sai Ma, Vista; Srinivasa Rao, Laguna Niguel, both of Calif.

[73] Assignee: Biomerica, Inc., Newport Beach, Calif.

[21] Appl. No.: 447,382

[22] Filed: May 23, 1995

Related U.S. Application Data

[63] Continuation of Ser. No. 268,299, Jun. 30, 1994, abandoned, which is a continuation of Ser. No. 132,055, Oct. 5, 1993, abandoned, which is a continuation of Ser. No. 798,638, Nov. 26, 1991, abandoned.

[51] Int. Cl.$^6$ .................... G01N 33/564; G01N 33/543
[52] U.S. Cl. .................... 436/506; 435/7.21; 436/518; 436/811; 436/827
[58] Field of Search .................... 436/506, 518, 436/811, 827; 435/7.21

[56] References Cited

PUBLICATIONS

Tsuji et al., Binding of islet cell cytoplasmic antibody from insulin-dependent diabetes mellitus patients and plant lectin (Maclura pomifera agglutinin) to pancrease islet cells, Biol. Abstr. 83(6):54630, 1987.

Kitagawa et al., Detection of islet-cell-surface antibodies by using 125I-labeled wheat germ agglutinin (125I-WGA) bound islet-cell protein, Chem. Abs. 103:176674g, 1985.

Baekkeskov et al., Autoantibodies in newly diagnosed diabetic children immunoprecipitate human pancreatic islet cell proteins, Nature 298:167–169, 19982.

Doyle et al., Applications of Lectins in Microbiology, ASM News 55(12):655–658, 1989.

Allergy Immunotechnologies, Inc., Isletest–ICA Qualitative Test for Detection of Circulating Antibodies Against Islet Cell Atnigens, 1989.

*Primary Examiner*—Marian C. Knode
*Assistant Examiner*—Donna C. Wortman
*Attorney, Agent, or Firm*—James A. Quinton

[57] ABSTRACT

An in vitro diagnostic test for analyzing body fluid so as to obtain an indication of the risk of developing insulin dependent diabetes-mellitus (IDDM) is provided. A solid phase containing immobilized pancreatic antigens is contacted with a test sample. The solid phase includes a water insoluble polymer carrier, a lectin attached to the water insoluble polymer, and mammal derived pancreatic proteins. The pancreatic proteins include pancreatic antigens which are reactive to islet cell autoantibodies which are routinely detected in the blood of patients who have recently been diagnosed as having insulin dependent diabetes mellitus (IDDM). A test sample is incubated with the solid phase containing immobilized pancreatic antigens for a sufficient time to allow a reaction between the immobilized pancreatic antigens and autoantibodies to the pancreatic antigens in the sample to bind the autoantibodies to the solid phase. Detectably labelled molecules which are selectively reactive to human IgG are then added and incubated with the solid phase for a sufficient time to allow the reaction of the labelled molecules with the bound antibodies to the pancreatic antigens to thereby attach the labelled molecules solid phase.

26 Claims, No Drawings

DIAGNOSTIC TEST FOR MEASURING ISLET CELL AUTOANTIBODIES AND REAGENTS RELATING THERETO

This application is a continuation application of Ser. No. 08/268,299 filed Jun. 30, 1994, abandoned, which is a continuation application of Ser. No. 08/132,055 filed Oct. 5, 1993, abandoned, which is a continuation application of Ser. No. 07/798,638, filed Nov. 26, 1991, abandoned.

FIELD OF THE INVENTION

The present invention relates to the detection of Islet Cell Autoantibodies. The presence of islet cell autoantibodies (ICA) has been found to be an indication of the susceptibility of a non-diabetic patient to developing insulin dependent diabetes mellitus (IDDM). It has been found that the prevalence of islet cell antibodies (ICA) in insulin dependent diabetes if tested about the time of the onset of diabetes is very high. For example, if the test is done within the first one or two weeks of the onset of symptoms, up to 85% of diabetic children will have detectable islet cell antibodies (ICA). Clinical Immunology, Parker, P. 836 (1980). The present invention relates to a simple in vitro serodiagnostic method of detecting islet cell antibodies.

DESCRIPTION OF THE PRIOR ART

The presence of autoantibodies against islet cell antigens is considered an indication of autoimmune reaction and subsequently to a later development of IDDM. (Eisenbarth et al., Diabet/Metab Rev., 3:873, (1987); Srikanta etal., Diabetes, 35:139, 1986; Kamalesh and associates, Pract. Cardiol., 12:79, 1986; Riley et al., Adv. Pedtiatr., 35:167, (1988). In the prior art, serum ICA has been determined by indirect immunofluorescence and histochemical methods employing frozen unfixed human/primate or rat pancreatic sections as substrates. Despite various attempts to improve the sensitivity and specificity by modifying this procedure since its original description in 1974, the indirect immunofluorescence/histochemical technique suffers from inherent methodological problems. See: Bottazo, F. G., A. Florin-Christense, and D. Doniach (1974), Islet Cell Antibodies in Diabetes Mellitus with Polyendocrine Deficiencies, Lancet, II:1279–1283; Srikanta, S., A. Rabizadeh, M. A. K. Omar, and G. S. Eisenbarth (1980), Assay for Islet Cell Antibodies: Protein A-Monoclonal Antibody Method, Diabetes, 34:300–305. Standardization of the technique has proven to be very difficult. The reliability of this "frozen-section" technique is limited by factors such as the variation from one pancreas to another, the inevitable need for unfixed pancreatic tissue and the infrequent availability of the suitable tissue. Consequently, there is a need in the prior art for a simple reproducible test for ICA that can be performed without access to fresh human pancreas.

It has been shown in the prior art that a 64,000 (64 KD) molecular weight (MW) protein is consistently recognized by IDDM autoantibodies. It has been suggested that a convenient clinical assay awaits its isolation, purification and primary structure determined by microsequencing Kiechle, F. L., Malinski, T., Moore, K., Insulin Action: Implications for the Clinical Laboratory, Laboratory Medicine, 21:9, 565–73 (1990). Recently the nature of the 64 KD protein has been suggested. See, Baekkeskov, S., Aanstoot, H. K., et al., Identification of the 64K Autontigen in Insulin-Dependent Diabetes, Nature 347, 151–55 (1990).

Sandwich type diagnostic tests are well known in the prior art, e.g., the RAST test for IgE, see U.S. Pat. No. 3,720,760. Sandwich tests typically employ a marked reagent such as anti-IgE in the RAST test. The marker can be a radioactive isotope, an enzyme, fluorescein or other suitable detectable label.

Lectins are divalent or multivalent carbohydrate binding proteins grouped together because of their ability to agglutinate erythroctyes and malignant cells. The lectin receptor on the cell membrane is usually the terminal or the adjacent sugar bound to proteins or/and lipids.

Naturally occurring lectins have been isolated from a wide range of plants and animals (Gold and Balding, Receptor Specific Proteins: Plant and Animal Lectins, Excerpta Medica Amesterdam, 1975; Cohen and Vista, In Developmental Immunology, Clinical Problems and Aging, Cooper and Brazier, eds, Acad. Press, N.Y., 1982). Concanavalin A (Con A) is a lectin which can be isolated from the Jack bean, see, Sumner and Howell (J. Bacteriol, 32:227 1936).

Lectins have been used in affinity purification of proteins. For example, proteins from various sources have been purified using lectin affinity chromatography. Lectin have been used in purifying both the cell wall and cytoplasmic microbial antigens. Nghiem, Eur. J. Biochemistry, 75:613 (1977) purified the two cell wall antigens from Salmonella Zuerich using Con A. Cytoplasmic antigens for serodiagnosis of Paracoccidioidomycosis were prepared using Con A affinity chromatography by Mcgowan and Buckley (J. Clin. Microbiology, 22:39, 1985). In this study, the fraction of the cytoplasmic extract of Paracoccidioides brasiliensis that binds Con A was found to be the antigen recognized by antibodies in patients' sera.

Concanavalin (Con A) is a lectin which has been found useful as a purification tool for proteins. Con A generally binds to saccharides containing ..D-mannose or ..D-glucose residues So and Goldstein, J. Immunol., 99:158, 1967; J. Biol. Chem., 242: 1617 (1967). It recognizes both the terminal and internal protein saccharide residues Goldstein et al, Biochemistry, Biochem. Biophys. Acta., 317:500, 1973).

Con A has been used for the removal of nonspecific antigens from microbial extracts. Greenfield and Jones, Infection and Immunity, 34:469 (1981) purified the cytoplasmic antigens of Candida albicans by selectively adsorbing the nonspecific cell wall mannan on to the lectin column. The portion of the yeast extract that did not bind to Con A was found to be the mixture of antigens—specific for C. albicans. Similarly a platelet antigen specific for antibodies from quinidine purpura was purified using a wheat Germ Agglutin column.

Antigens/allergens of plant origin have also been purified using the lectin affinity chromatography technology. Allergenic glycoproteins from peanut have been purified using a combination of ion-exchange, gel permeation and affinity chromatography. Barnet and Howden (Biochem. Biophys. Acta, 882:97, 1986) purified a Con A reactive 65KD peanut protein that was found to be potent allergen for peanut-sensitive patients.

Purification of antibodies also has been assisted by the use of lectin. The carbohydrate residues on the Fc portion of the antibody molecule bind the lectin. Biewenja etal. Molecular Immunology, 256:C865, (1989), purified IgA and its fragments using a Jacalin-sepharose. Jacalin is an N-terminal galactose specific lectin. IgA and its fragments were precipitated by Jacalin bound sepharose.

SUMMARY OF THE INVENTION

It has been found that islet cell autoantibodies (ICA) can be found in over seventy (70%) percent of recently diagnosed IDDM patients. The susceptibility to the development of IDDM has been linked to the presence of such antibodies in the blood. Thus, according to the invention a simple diagnostic test has been developed which is based on a solid phase having immobilized pancreatic antigens which will be recognized by islet cell autoantibodies of sera from clinical and/or preclinical IDDM patients but do not contain antigens that is recognized in healthy patient sera.

In another aspect of the invention, it has been found that there are at least four pancreatic antigens to which islet cell autoantibodies are directed. Thus, it is desirable to have a diagnostic test for ICA which responds to at least one of these pancreatic antigens. To minimize false negatives in a diagnostic test, it is desirable that the test recognize the presence of two or more of those antibodies and preferably three or four.

Another aspect of the invention is a simple method to manufacture reagents used in such a diagnostic test and to provide a storage stable pancreatic antigen solid phase. Because antigen isolation and purification can be an expensive and time consuming process, it is most desirable to avoid complicated isolation and purification procedures for the four pancreatic antigens which are reactive to ICA and directly fix the pancreatic antigens onto an insoluble carrier without first isolating and purifying the proteins.

It is an object of the invention to provide a diagnostic test for ICA.

It is an object of the invention to provide a diagnostic test that gives an indication of the susceptibility of a patient to develop IDDM.

It is an object of the invention to provide a diagnostic test that can detect more than one autoantibody to islet cell antigens.

It is an object of the invention to provide a storage stable solid phase containing pancreatic antigens which can be used to determine the presence of ICA in a human body fluid such as blood or serum.

It is an object of the invention to provide a method of fixing pancreatic antigens which react to ICA, to a water insoluble carrier without prior isolating and/or purifying individual pancreatic antigens.

Other additional and further objects will become apparent from reading the following specification of the invention.

According to the invention, a diagnostic test has been developed for a determination of ICA in a body fluid. In particular a test has been developed which gives ax positive response to serum from patients who have been confirmed as recently developing IDDM and a negative response to healthy patient sera. In another aspect of the invention a test which responds to the presence of two or more of the antibodies to pancreatic antigens which have been identified as present in newly diagnosed IDDM patients and hence, give an indication of susceptibility to later development of IDDM is provided. In addition, a simple method of preparing reagents for use in the test has been developed. The resulting diagnostic test is fast, direct, reliable, reproducible and highly sensitive. Moreover, with proper controls the test can be used to give a quantitative readout of the amount of ICA antibodies present in a given sample.

According to the invention a sandwich type immunosorbent diagnostic test is provided. First, pancreatic antigens are immobilized to a water insoluble polymer carrier. The preparation of the polymer carrier is accomplished by attaching a lectin, preferably Concanavalin (Con A) to the water insoluble polymer with bonds that are capable of withstanding normal washing procedures, e.g., the Con A can be absorbed to the carrier or covalently bound thereto. Mammal pancreatic antigens are then attached to the immobilized Con A by bonds capable of withstanding normal washing procedures.

The mammal pancreatic antigens are preferably derived from rodent or human pancreas. Desirably, the pancreatic antigens include at least two and preferably four or more pancreatic antigens that react to antibodies routinely detected in the blood of patients who have been recently diagnosed as IDDM. Desirably the polymer carrier is a plastic polymer microtiter plate. However, many water insoluble polymers will suffice. Such carrier may be in the form of paper or plastic disks or strips, or plastic beads, plastic microtiter plates, microwells, or plastic and nitrocellulose membranes or membranes coated with charged resins. The lectin may be absorbed to the polymer carrier or linked thereto by covalent bonds.

Desirably after the pancreatic antigens have been attached to the lectin (preferably Con A) carrier conjugate, a blocking protein is added to block off any unbound lectin protein binding sites remaining after incubation with the pancreatic antigens. This blocking protein should be non-reactive to human immunoglobulins.

The polymer carrier—lectin—pancreatic antigen conjugate is then used as the solid phase in an immunoassay. A sample typically a body fluid from a patient such as blood most desirably serum is incubated with the pancreatic antigen conjugated carrier for a sufficient time for the antibodies in the sample to attach to the pancreatic antigens attached to the carrier phase.

The sample is then washed to remove any unbound sample proteins. Antibodies to human IgG which have been labelled are added to the solid phase and incubated for sufficient period of time for the labelled antibodies to react with the antibodies immunologically bound to the pancreatic antigens. The resulting solid phase is then washed and the amount of labelled antibodies that have been attached is measured. As a result an indication of the presence of ICA is obtained and a determination of the patient's susceptability to IDDM can be predicted.

The preferred embodiment of the present invention is illustrated in appended detailed description of the invention and in the Examples. However, it should be expressly understood that the present invention should not be limited solely to the illustrative embodiment.

DETAILED DESCRIPTION OF THE INVENTION

In accordance with the present invention it has been found that an effective solid phase for use in the diagnostic testing for the susceptibility of patients to developing to IDDM is provided by binding a lectin preferably Con A to a water insoluble polymer then binding thereto a mammal preferably rodent or human pancreatic antigen desirably rat pancreatic antigens to form a water insoluble polymer-lectin-antigen conjugate.

In another aspect of the invention, a reproducible direct fast, reliable and highly sensitive diagnostic test is provided using the water insoluble polymer-lectin, (preferably Con A), mammal and/or rodent pancreatic antigen conjugate in a sandwich type immunosorbent test.

According to the invention the mammal preferably rodent or human pancreatic antigens which respond to ICA found in recently diagnosed insulin dependent patients and which do not respond to antibodies in healthy patient serum are conjugated to a polymer carrier-lectin conjugate to form a solid phase for the diagnostic test. The resulting diagnostic test gives a positive indication when tested against recently diagnosed IDDM positive patients and a negative indication to healthy patient serum. Preferably the test according to the invention responds to two or more of the antibodies which react to islet cell antigens and which are present in newly diagnosed IDDM patients. Thus, the diagnostic test according to the invention gives a good indication of the susceptibility of the patient to later development of IDDM. According to the invention some of the pancreatic antigens to which islet cell autoantibodies are directed have been identified. A type-O human pancreatic extract was subjected to SDS-PAGE. Western Blot using a panel of clinically confirmed recently diagnosed IDDM patient sera was performed. A Western Blot using a panel of clinically confirmed negative IDDM sera was also performed. A positive and negative IDDM sera pool was made from these panels. A total of 4 islet cell antigens having molecular weight of about 90 KD, 67 KD, 59 KD and 34 KD can be routinely identified as reactive to the islet cell autoantibodies from such pool. Two major protein bands (67 KD and 59 KD) are identified by about 70% of the sera panel. The third major band (90 KD) is identified by 50% of the sera panel. One minor band (34 KD) was recognized by 80% of the panel.

According to the invention an easy to prepare, storage stable, water insoluble carrier is provided for use in a diagnostic test to determine islet cell autoantibodies (ICA) and hence, obtain an indication of the susceptibility of a patient's later development of IDDM. This solid phase reactant includes a water insoluble polymer such as paper, plastic, e.g., polystyrene, polypropylene or the like. The water insoluble polymer can be in the form of paper disk or paper strips, microtiter beads composed of polystyrene or the like or preferably microtiter wells composed of polystyrene such as microtiter plates supplied by Costar Corp., Kennebunkport, Me. Such plates typically have a number of wells supplied in plate and in strip fashion.

To the microtiter wells, a lectin preferably Con A is attached by bonds capable of withstanding normal washing procedure. The lectin may be attached to the water insoluble polymer by covalent bonds through methods well known in the art such as CNBr linkage to paper disks and other methods of conjugating proteins to water insoluble polymers. Preferably lectin is adsorbed to microtiter plates which are desirably composed of polystyrene. The lectin is attached to the microtiter plates for example by incubating a solution of Con A at a low temperature preferably from 2° C. to 8° C. in the microtiter plate wells for a sufficient time to bind the Con A to the microtiter plate. Typically an incubation time of 8 to 15 hours is used and preferably overnight.

The Con A can be obtained from numerous commercial sources such as Cal Biochem and is readily available on the market. The Con A solution is obtained by dissolving commercial Con A, for example, Cal Biochem No. 234567 in a buffered saline preferably a phosphate buffered saline (PBS) having a pH of from 5 to 8 desirably a pH of 6.5. The final solution is from about 1 ug/ml to 1.5 mg/ml, preferably about 0.5 mg/ml (500 ug/ml).

A sufficient amount of the Con A solution is then dispensed into the microtiter plates and incubated preferably overnight at a temperature of from 2° C. to 8° C. preferably at about 4° C. Preferably 100 ul/well of Con A solution is used when for example Costar microtiter plates are used. The lectin containing microtiter wells are then incubated for a sufficient period for the lectin to be absorbed by the polystyrene micro wells. Unbound lectin solution is then decanted from the microtiter plate. The plates are preferably blotted dry. The resulting microtiter well Con A conjugate is then ready for attachment of pancreatic antigens.

According to the invention, pancreatic antigens are attached onto the microtiter wells Con A conjugate. Preferably mammal pancreatic antigens are used. The pancreatic antigens may be derived from human pancreas particularly human pancreas of the type-o blood type. Since human pancreas are in short supply, it is preferable to use mixed and/or other sources of pancreas which are more readily available for example, rodents. Preferably rat pancreas are used. Desirably rat pancreas from immune deficient rat strains are used. For example, the BB strain of rat maintained by the University of Massachusetts, optionally pancreas from the non obese diabetic mouse (ND rat) and Wistar Albino rat strain have also been found as a useful pancreas antigen source for use in the invention. It has been found that these rat pancreas include pancreatic antigens that are reactive to ICA. In addition, such pancreatic antigens have been found non-reactive to other immunoglobulins found in human blood serum e.g., healthy normal serum, with high titer of thyroid autoantibodies and even rheumatoid factors.

In selecting a mammal preferably rodent, most preferably rat strain for use in accordance with the invention, one needs to screen a typical pancreas from the strain or species. The pancreas of each suspected strain and/or species is carefully dissected out, washed in cold PBS and cut into small pieces. An extract is prepared by suspending one gland in 2–5 ml of cold PBS, homogenized briefly in ice bath and sonicated briefly in ice bath. A detergent (octyl-B-D-glucopyranoside) is then added. After removing debris by centrifugation, protein concentration of extract is determined. The extract is subjected to standard SDA-PAGE with the appropriate molecular weight (MW) marker proteins. A standard pancreatic extract is used as positive control standard. The standard IDDM positive sera pool is used in Western Blot. The SDS-PAGE and Western Blot of the suspected species and the standard are compared carefully. Extracts that produce one or more bands with clinically confirmed IDDM positive sera pool but not with the IDDM negative sera pool will be selected. Desirably, the extract should produce two or more confirmatory bands, preferably at least a 59 KD and 67 KD bands and most preferably a pancreas that includes 90 KD, 59 KD, 67 KD and 34 KD proteins. Such pancreas can then be used as a source of pancreatic antigens for binding to a water insoluble carrier-lectin conjugate. The solid phase for use in the diagnostic test according to the invention is prepared by binding suitable pancreatic antigens, screened as described above, to a water insoluble polymer lectin conjugate.

Preferably a rat pancreas from a suitable rat strain is prepared for a fixation to the lectin preferably Con A, water insoluble polymer conjugate. Suitable rat pancreas preferably pre-frozen are washed in a cold saline solution preferably PBS having a pH of about 7. The tail end portion of clean glands are cut into small pieces and suspended in a cold saline solution preferably PBS in an amount of 1 gland per 10 ml of suspension solution. The glands are then homogenized preferably in an ice bath for a sufficient period until complete homogenation is obtained. Typically, the homogenization will take from 1 to 2 minutes. The homogenized preparation is then sonicated in an ice bath for a sufficient time to insure that there are no tissue lumps remaining. Desirably sonication should be performed for 15 to 60 seconds, preferably about 30 seconds.

Desirably a non ionic detergent is added to the pancreatic homogenate. Preferably a detergent such as octyl-B-D glucopyranoside for example, supplied by Cal Biochem is added to the pancreatic homogenate. Desirably a final detergent concentration of 0.5 to 5% is obtained and preferably about 2%. Desirably the detergent solution is prepared with a detergent concentration of 10 to 30% and preferably about a 20%. Preferably the resulting detergent solution is then added to the homogenate and the mixture stirred to assure complete mixing preferably for from 30 to 90 minutes, desirably for about 60 minutes at low temperature preferably at 2° to 8° C. The resulting mixture is then centrifuged at high speed (preferably at about 10.000×G for 10 to 30 minutes most preferably 20 minutes). The supernate is collected and the protein concentration of the supernate is then measured using a protein assay for example, the Bio-Rad protein assay. The resulting extract can be frozen at a temperature of from −10° to −30° C. preferably −20° C. for later use.

The lectin insoluble polymer preferably polystyrene microtiter well Con-A conjugate is incubated with a sufficient amount of a suitable pancreatic extract for a sufficient period of time so that substantial amounts of pancreatic antigens are linked to the lectin water insoluble polymer carrier. For example, frozen pancreatic extract as described above is thawed and centrifuged at high speed to remove any insoluble material. Based on the prior assay of protein concentration, the extract is diluted, preferably with saline, desirably a buffered saline such as PBS at a pH of about 7 to a final protein concentration of from 10 to 1,000 ug/ml, preferably 200 to 400 ug/ml and desirably 300 ug/ml. Preferably polystyrene wells to which Con A has been conjugated are incubated with a sufficient amount of rat pancreatic extract preferably immune deficient rat pancreatic extract most desirably BB rat strain pancreatic extract in an amount of about 100 ul/well of diluted pancreatic extract. This amount of course can be varied depending on the size of the well and binding capability of the particular microtiter plate.

The pancreatic extract is then incubated in the microtiter well for sufficient time for the pancreatic antigens to conjugate with the available lectin preferably Con A binding sites. Desirably this incubation is continued overnight at low temperatures preferably at about 4° C. Subsequently, the next morning any unbound pancreatic extract is drained from the plates.

Preferably unbound lectin sites are then blocked preferably by adding a protein blocking agent which is non-reactive to human IgG. Preferably where Con A is the lectin, a 10% dialysed goat serum (delipidized) is added to the microtiter wells that have been previously conjugated with the pancreatic antigens and incubated at low temperature preferably 2° C. to 8° C. for a sufficient time, desirably 12 to 24 hours preferably overnight so that blocking proteins preferably the goat serum proteins bind with the unbound lectin (Con A) sites. The blocked microtiter plates are then washed to remove any unbound goat serum. Desirably the blocked microtiter plates are washed three times with PBS preferably PBS containing tween 20 (PBST) and stored at low temperature. The resulting conjugate is storage stable and ready for use as the solid phase in a diagnostic test.

Any sample suspected of containing ICA may be tested according with the methods set forth herein. Most particularly body fluids such as blood or serum may be used for test samples. According to the invention, a sample is incubated along with the prior prepared solid phase reactant as heretofore described. Desirably the solid phase is the polystyrene microtiter well having a Con A rat pancreas antigen conjugated thereto. Desirably serum is used in the sample, preferably the serum sample is diluted in PBS or PBST or other suitable diluents. Desirably a 1 to 100 dilution is performed of serum sample, thus, for example 25 ul (0.25 ml) of serum sample are added to a 2.5 ml of diluent buffer. Preferred diluents and dilution ratios may vary from sample to sample. Simultaneously with the running of any sample, it is preferable that both negative and positive controls be also run.

The sample is added to the microtiter wells and incubated for a sufficient period to allow conjugation of any islet cell autoantibodies in the sample with the pancreatic antigens attached to the solid phase. Typically such incubation should be performed from one half to two hours at room temperature most desirably for one hour. After incubation, unconjugated blood serum is washed from the solid phase. Desirably if a microtiter well is used, the wells are filled with a wash solution and blotted dry. Preferably the wash procedure is repeated several times to insure complete removal of any unconjugated serum.

In accordance with the invention the islet cell autoantibodies (ICA) are detected by contacting the ICA which have been immobilized to a solid phase with a detectably marked or labelled antibody specific for human IgG or other human IgG binding proteins. The marker or label for such protein can be selected from radioactive isotope, enzyme label, a fluorescent label or other detectable labels. Preferably an enzyme label is used. When an enzyme label is used, an appropriate substrate is added after incubation with the enzyme labelled antibodies. Typically enzymes are horse radish peroxidase or alkaline phosphatase enzyme. The enzyme substrates can be tetramethyl benzidine and p-nitrophenyl phosphate respectively.

After the solid phase has been incubated with the sample and washed, a detectably labelled anti-human immunoglobulin is added. Preferably an anti-human IgG enzyme conjugate is added to the solid phase immune complex, preferably to a microtiter well and incubated at room temperature for a sufficient time for the immune reaction of the anti-human immunoglobulins with the immobilized ICA that have attached to the solid phase. Desirably such incubation is performed for from one half hour to two hours and preferably for about one hour at room temperature. After incubation, each plate is blotted dry and washed preferably with a buffer solution. Desirably the washing procedure is repeated at least three times. Preferably, the plates are then further blotted dry. In the case where an enzyme label is used, an enzyme substrate reagent is added to the microtiter wells. The plates are incubated for 10–30 minutes depending on the nature of the enzyme and substrates used. The absorbance of the various samples is measured and compared with both negative and positive controls.

EXAMPLES

Example 1

Preparation of the Pancreatic Extract

According to the invention a pancreatic extract is prepared from a suitable rat species such as BB rats. First, ice cold phosphate buffered saline (PBS) having a PH of 7 is prepared. Prefrozen BB rat pancreas are then washed in the ice cold PBS. The washed glands are then cut into small pieces and the small pieces are suspended in ice cold PBS in an amount of 1 gland per 10 milliliter liters of PBS. The glands are then homogenized in an ice bath for 1 to 2 minutes until a homogeneous preparation is made. This homogeneous preparation is then sonicated for 30 seconds. Care should be taken that there not be any tissue lumps remaining.

A fresh 20% solution of detergent octyl-B-D-glucopyranoside, e.g., Cal Biochem, 49445, is added to the pancreatic homogenate so that a final detergent concentration of 2% is obtained. The mixture is then stirred for 20 minutes at 2 to 8 degrees C. The resulting mixture is then centrifuged at 10,000×G for 20 minutes. The supernatant is then taken and the protein concentration is measured using the BIO-RAD Assay. The extract is then frozen at minus 20° C.

Example 2

Preparation of ICA Plates

Concanavalin A (Con A) is attached to a microtiter plate having microtiter wells composed of a polystyrene plastic supplied by Costar Corp., Kennebunkport, Me. A solution of Concanavalin A is added to the microtiter plates and incubated overnight at 4° C.

The Con A solution is prepared by dissolving Con A obtained from Cal. Biochem. (No. 234567) in PBS pH 6.5 to obtain a final concentration of Con A of about 0.5 mg. (500 ug) per ml. 100 ul/well of the Con A solution is dispensed in the microtiter plates and incubated overnight at 4° C. The next morning the rat pancreatic extract from Example 1 above is thawed and centrifuged at high speed to remove any insoluble material. The extract is then diluted in PBS (pH 7.0) to a final protein concentration of 300 ug/ml. Unbound Con A is then decanted from the microtiter plates which have sat overnight in contact with the Con A solution to form a conjugate between the Con A and the microtiter plates. The plates are blotted dry using paper towels. These blot dried plates are then immediately used.

A 100 ul per well of the diluted pancreatic extract is dispensed into Con A conjugated plates and incubated overnight at 4° C. The next morning any unbound pancreatic extract is removed from the plates.

Unbound Con A sites are then blocked with a 10% dialysed goat serum (delipidized) and incubated overnight at 2°–8° C. The blocked microtiter plates are then washed three times with PBS containing tween 20 (PBST). The resulting plates are then kept in airtight plastic zip-lock bags then assigned a lot number and kept at 2°–8° C. until used. The prepared solid phase islet cell antigen plates are stable when stored 2°–8° C. for 6 month for later use in the diagnostic test.

Example 3

Test Procedure

Microtiter wells prepared in accordance with the invention are assembled. A positive and negative control are run simultaneously with the test sample. The wells are assigned an indexing system for example: A1 to H1, A1 and B1 can be used for blanks for microtiter reader plate blanking, C1 and D1 can be used for negative control, and E1 and F1 for positive control and G1 and H1 for a single test sample. Additional wells can be used if more than one sample is tested.

Samples are added to the microtiter plates. For example, 100 ul of a negative control is dispensed into microwells C1 and D1. 100 ul of a positive control is dispensed into microwells E1 and F1. 100 ul of diluted patient serum is added to microwells G1 and H1. For more patient samples, additional microtiter wells are used in duplicate. There should be 100 ul of solution in each microwell to be assayed except A1 and B1 which are empty at this point and will be used later.

Each plate is covered with a parafilm/plastic wrap (to prevent contamination) and held for 1 hour at room temperature. After incubation, each plate is blotted dry by tapping gently onto a paper towel a few times to discard the solution from all wells. Washing can be done manually or by an automatic plate washer. In such instance each well is washed with 300 ul (0.3 ml) of wash. When a squeeze bottle is used the wells are filled with the wash solution and then the buffer is drained from the microwells. This washing procedure is repeated three more times. The plates are then blotted dry with a paper towel. Thereafter, 2 drops of anti-human IgG Alkaline Phosphatase Conjugate reagent is added to all microwells except wells A1 and B1. Each plate is then covered with a parafilm/plastic wrap incubated at room temperature for one hour. The wells are further washed three times and two (2) drops of a freshly prepared enzyme Substrate Reagent (p-nitrophenyl phosphate) are added to all microwells including wells A1 and B1. The plates are incubated in the dark for 30 minutes at room temperature.

A microtiter plate reader is then set up to read at 405 nm absorbance, according to manufacturer's instructions. Thirty (30) minutes after substrate addition, one drop of the stopping solution is added into each well as quickly as possible. The plate reader is blanked using A1 or B1 wells and the absorbence of the plates is read at 405 nm. The results of the test are calculated as follows:

Calculation of Data

The spectrophotometric readings [optical density (OD) in absorbance units] is recorded. The average reading of a sample or control done in duplicate is calculated as follows:

Average reading of the sample (Av)=(1st OD+OD)/2. The average reading of the negative control data is N Avg. positive control data is $^P$ Avg. and sample data is $^S$ Avg. The cut-off point (X) of each run is calculated as follows:

$$\text{Cutoff Point } (X) = ^N Avg. \times 2.5$$

The specification (Y) of each run is calculated as follows:

$$\text{Specification } (Y) = ^N Avg. \times 3$$

A (+) and (−) is entered by comparing the average sample (S) OD value with the calculated cut-off point value. The weak positive patients or borderline cases (5% above the cut-off point) should be tested again after 6 months along with the previous serum sample as a reference.

Positive and negative controls should be run along with unknown samples each time for results to be valid.

A negative control O.D. reading greater than 0.3 of positive control reading or less than 3 times the negative O.D. signifies invalid results. Such results should not be reported. The test should be repeated.

| Data from a Typical Test Run is Reported Below | | | |
|---|---|---|---|
| Section A: Control Results | | | |
| Controls | Data O.D. | Ave. O.D. | Cut-off Value X  X = (2.5 × $^N$ Avg.) |
| Negative | 0.245  0.233 | $^N$ Avg. = 0.239 | X = 0.597 |

Interpretation:
1. For a valid test, $^N$ Avg. < 0.5. Repeat the test if results are not valid.
2. ICA-Positive Result: Average Sample O.D. ($^S$) Avg. > X.
3. ICA-Negative Result: Average Sample O.D. ($^S$) Avg. < X.

-continued

Data from a Typical Test Run is Reported Below

Section B: Patient Sample Results

| Patient | Data O.D. | Ave. O.D. | Results (Cut-off Point: X = 0.597) | |
|---|---|---|---|---|
| | | | Positive (+) (Ave. O.D. > X) | Negative (−) (Ave. O.D. < X) |
| 1 | 0.225 0.229 | $S_1$Avg. = 0.227 | | − |
| 2 | 0.435 0.395 | $S_2$Avg. = 0.415 | | − |
| 3. | 0.788 0.832 | $S_3$Avg. = 0.810 | + | |
| 4. | 0.662 0.668 0.832 | $S_4$Avg. = 0.665 | + | |

Example 4

Performance Characteristics and Correlation with Tissue Staining Technique

The specificity of BB rat pancreatic antigen coated microwell strips according to the invention was established by Western Blot analysis using confirmed IDDM patients' sera. Patients with thyroid autoantibodies and rheumatoid factors read negative.

50 serum samples were tested and found to be ICA-positive by the immunofluorescent tissue staining technique. The ICA test method according to the invention showed 90% correlation with the tissue staining technique for ICA-positivity. In addition, of the fresh onset IDDM patients, about 80% were found to be ICA-positive by the method according to the invention.

Example 5

Rat Pancreas Selection

Rat pancreas are screened for suitability as follows:

A fresh pancreas is washed after dissection of a BB rat. The tail portion is cut into small pieces, mixed with 10 milliliter of cold PBS, the mixture is homogenized in an ice bath for one minute and then sonicated for 30 seconds. Octyl-B-D-glycopyranoside is added to a final concentration of 2%. The resulting mixture is centrifuged at 10,000×G for 20 minutes. The protein concentrate is determined by Bio-Rad assay. 10 ug of the sample pancreatic extract and 10ug of a type-O human pancreatic extract with suitable molecular weight markers are subjected to SDS-PAGE. The resulting gels are subjected to Western Blot using 1:100 dilution of clinically confirmed IDDM positive sera pool and negative sera pool. The bands are visualized by anti-human IgG alkaline phosphatase labelled using nitro blue tetrazolium salt and 5-bromo-4-chloro-3 indoyl phosphate as substrate. The pancreatic extract that showed protein bands by Western Blot techniques using IDDM positive sera but not using IDDM negative sera are chosen. The Western Blot profile of the pancreatic extract is compared with positive control standard. The pancreatic extract had 90 KD, 67 KD, 59 KD and 34 KD protein bands and thus is suitable for use according to the invention.

It should be understood by those skilled in the art that various modifications may be made in the present invention without departing from the spirit and scope thereof, as described in the specification and defined in the appended claims.

We claim:

1. An immobilized antigen-containing solid phase suitable for use in detecting the presence of islet cell autoantibodies, ICA, in a sample comprising:

a water insoluble polymer;

concanavalin A, Con-A, attached to said water insoluble polymer with bonds capable of withstanding normal washing procedures;

mammal-derived pancreatic proteins attached to said Con-A by bonds capable of withstanding normal washing procedures, said pancreatic proteins including pancreatic antigens which selectively bind to islet cell autoantibodies, which autoantibodies are routinely detected in the blood of patients who have recently been diagnosed as having insulin-dependent diabetes mellitus, IDDM;

non-human blocking proteins attached to substantially all Con-A binding sites which are not bound to pancreatic antigens, said blocking proteins being non-reactive to human IgG and anti-human IgG.

2. A solid phase according to claim 1 wherein the mammal-derived pancreatic antigens are derived from rat pancreases that contain antigens that specifically bind to at least two (2) different islet cell autoantibodies detected in newly diagnosed IDDM patients, said autoantibodies reactive with two or more pancreatic antigens having a molecular weight of about 90 KD, 67 KD and 34 KD.

3. A solid phase according to claim 2 wherein the rat strain is an immunodeficient rat strain.

4. A solid phase according to claim 2 wherein the rat strain is selected from the group consisting of BB strain, N.D. strain and Wistar Albino strain.

5. A solid phase according to claim 1 wherein the mammal-derived pancreatic antigens are rat pancreatic antiaens and specifically bind to four (4) islet cell autoantibodies, ICA, detected in newly diagnosed IDDM patients, said autoantibodies reactive with a 90 KD islet cell antigen, a 67 KD islet cell antigen, a 59 KD islet cell antigen and a 34 KD islet cell antigen.

6. A solid phase according to claim 5 wherein the water insoluble polymer is a polystyrene microtiter plate.

7. A solid phase according to claim 6 wherein said blocking proteins are goat serum proteins.

8. A diagnostic test kit according to claim 7 wherein the detectable label is selected from the group consisting of enzyme, radioactive isotope and fluorescent molecule.

9. A diagnostic test kit according to claim 8 wherein said water insoluble polymer is a polystyrene microtiter plate.

10. A diagnostic test kit according to claim 9 further comprising positive and negative control sera.

11. A diagnostic test kit for obtaining an indication of the risk of developing IDDM comprising an immobilized antigen-containing solid phase according to claim 1 and detectably labelled anti-human IgG.

12. A diagnostic test kit according to claim 11 wherein the detectable label is enzyme and said kit further comprises an enzyme substrate for activating said enzyme label.

13. An "in vitro" diagnostic test for analyzing body fluid so as to obtain an indication of the risk of developing insulin dependent diabetes-mellitus (IDDM) comprising:

i. contacting a solid phase containing immobilized pancreatic antigens with a test sample, said solid phase including:

a water insoluble polymer carrier;

Con-A attached to said water insoluble polymer with bonds capable of withstanding normal washing procedures, mammal derived pancreatic proteins attached to said Con-A by bonds capable of withstanding normal washing procedures, said pancreatic proteins including pancreatic antigens which are reactive to islet cell autoantibodies, said autoantibodies being routinely detected in the blood of patients who have recently been diagnosed as having insulin dependent diabetes mellitus, IDDM, wherein said pancreatic antigens are unreactive to antibodies in healthy patient serum; and blocking proteins which are non-reactive to human IgG and anti-human IgG attached to substantially all Con-A binding sites which are not bound to pancreatic antigens;

ii. incubating said test sample with said solid phase containing immobilized pancreatic antigens for a sufficient time to allow reaction between said immobilized pancreatic antigens and antibodies to pancreatic antigens in said sample to thereby bind said antibodies to said pancreatic antigens to said solid phase;

iii. adding to the product of step ii, molecules selectively reactive to human IgG, said molecules having a detectable label;

iv. incubating the product of step ii with said labeled molecules reactive to human IgG for a sufficient time to allow the reaction of said labeled molecules with said bound antibodies to said pancreatic antigens to thereby attach said labeled molecules to said polymer carrier;

v. removing any unreacted labeled molecules to human IgG;

vi. measuring the labeled molecules bound to said insoluble polymer carrier to obtain an indication of the risk of developing IDDM.

14. The "in vitro" diagnostic test according to claim 13 wherein the body fluid is human blood.

15. The "in vitro" diagnostic test according to claim 14 wherein the detectable label is an enzyme, a radioactive isotope or a fluorescent molecule.

16. The "in vitro" diagnostic test according to claim 14 wherein the water insoluble polymer carrier is selected from the group consisting of paper disks, paper strips, plastic microtiter plates, plastic beads, plastic membranes and nitrocellulose membranes.

17. The "in vitro" diagnostic test according to claim 14 wherein the pancreatic antigens are derived from an immunodeficient rat strain.

18. The "in vitro" diagnostic test according to claim 14 wherein the pancreatic antigens are derived from a rat strain selected from the group consisting of BB strain, N.D. strain and Wistar Albino strain.

19. The "in vitro" diagnostic test of claim 14 wherein the detectable label is an enzyme label.

20. The "in vitro" diagnostic test of claim 13 wherein the water insoluble polymer carrier is selected from the group consisting of paper disks, paper strips, plastic microtiter plates, plastic beads, plastic membranes and nitrocellulose membranes.

21. The "in vitro" test according to claim 13, wherein the mammal-derived pancreatic proteins are derived from a rat pancreas from a rat strain that contains antigens that specifically bind to at least two different islet cell autoantibodies detected in newly diagnosed IDDM patients, wherein said at least two different islet cell autoantibodies specifically bind to at least two different islet cell antigens selected from the group consisting of an about 90 KD islet cell antigen, an about 67 KD islet cell antigen, an about 59 KD islet cell antigen and an about 34 KD islet cell antigen.

22. The "in vitro" diagnostic test according to claim 21 wherein the rat strain is an immunodeficient rat strain.

23. The "in vitro" diagnostic test according to claim 21 wherein the rat strain is selected from the group consisting of the BB strain, N.D. strain and Wistar Albino strain.

24. The "in vitro" diagnostic test of claim 21 wherein said rat pancreas contains antigens that specifically bind to four (4) different islet cell autoantibodies detected in newly diagnosed IDDM patients.

25. The "in vitro" diagnostic test of claim 21 wherein said rat pancreas antigens includes four (4) antigens of different molecular weight.

26. The "in vitro" diagnostic test of claim 13 wherein the mammal is a rodent.

* * * * *